United States Patent [19]

Daunora et al.

[11] 4,193,766
[45] Mar. 18, 1980

[54] DEVICE AND METHOD FOR PREPARATION OF A CONTROL SOLUTION FOR KETONE DETERMINATION

[75] Inventors: Louis G. Daunora; Charles T. W. Lam; Myron C. Rapkin, all of Elkhart, Ind.

[73] Assignee: Miles Laboratories, Inc., Elkhart, Ind.

[21] Appl. No.: 959,693

[22] Filed: Nov. 13, 1978

[51] Int. Cl.² .................. G01N 33/16; G01N 21/48
[52] U.S. Cl. .......................... 23/230 R; 23/230 B; 23/930; 252/408; 356/213; 422/56
[58] Field of Search ............. 23/230 B, 930, 230 R; 422/56, 57; 252/408; 356/213

[56] References Cited

U.S. PATENT DOCUMENTS

| | | | |
|---|---|---|---|
| 2,186,902 | 1/1940 | Fortune | 23/930 X |
| 2,283,262 | 5/1942 | Kamlet | 23/930 X |
| 2,362,478 | 11/1944 | Galdt | 23/930 X |
| 2,509,140 | 5/1950 | Free | 23/930 X |
| 2,990,253 | 6/1961 | Smeby | 23/930 X |
| 3,912,655 | 10/1975 | Shukld | 23/230 B X |
| 4,078,892 | 3/1978 | Steinbrink, Jr. | 252/408 X |
| 4,097,240 | 6/1978 | Hirsch | 252/408 |

OTHER PUBLICATIONS

Chemical Abstracts, 69:56668r, (1968).
Chemical Abstracts, 78:154607, (1973).
Chemical Abstracts, 79:111473g, (1973).
Chemical Abstracts, 84:P127213, (1976).

*Primary Examiner*—Sidney Marantz
*Attorney, Agent, or Firm*—Edward H. Gorman, Jr.

[57] ABSTRACT

A device and method for preparing a ketone body control solution. The device comprises a carrier vehicle having incorporated with it a metal ion complex of a dione compound. The dione compound is characterized as having the structure

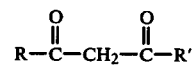

wherein R and R', same or different, are alkyl groups having 1 to about 6 carbon atoms. The method for preparing the control solution comprises contacting a predetermined volume of liquid with the device.

25 Claims, No Drawings

DEVICE AND METHOD FOR PREPARATION OF A CONTROL SOLUTION FOR KETONE DETERMINATION

BACKGROUND OF THE INVENTION

1. Field of the Invention

When a procedure is devised for determining the presence of a sample constituent—be the devised procedure gravimetric, volumetric, spectrophotometric or whatever mode—its efficacy in producing reliable results must somehow be assessed. Otherwise, the data developed is meaningless. Hence, devising such a procedure extends far beyond building a machine, formulating reagents or developing a technique. It also must of necessity include evaluating experimental error. There must be a way of predicting the dependability of the data produced by the procedure.

The easiest, most direct way to study parameters such as reproducibility, sensitivity, accuracy and need for calibration is to subject the procedure to a test sample wherein the analyte presence and/or concentration is known beforehand, i.e., a control solution. The data furnished by the procedure can then be compared with known data and any discrepancies properly noted.

The present invention concerns itself with assessing procedures for determining the presence and/or concentration of ketone bodies in a liquid sample. Moreover, it relates to a device for preparing a ketone control solution for use in assessing the performance of various ketone body determination procedures.

2. Description of the Prior Art

Acetoacetic acid (acetyl acetic acid) is a normal end product of fatty acid oxidation in the liver. It is also produced to a very limited extent by oxidative breakdown of leucine, phenylalanine, and tyrosine. β-hydroxybutyric acid is formed from acetoacetic acid by reversible reduction. Acetone is produced through non-reversible decarboxylation of acetoacetic acid.

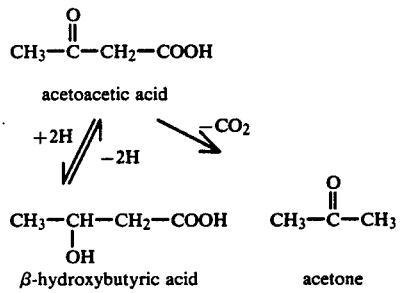

These three substances are commonly referred to as ketone bodies or acetone bodies.

Abnormally high amounts of ketone bodies in urine or blood are referred to as ketonuria and ketonemia, respectively. These conditions can occur as a result of such diverse pathological conditions as diabetes mellitus and starvation. Because of this disease/symptom relationship, especially with diabetes mellitus, there is keen interest in the determination of ketone bodies in urine. In the case of a diabetic, the detection of ketonuria is of great significance, since a change in insulin dosage or other disease management is often indicated. Thus, strong emphasis has been placed by the medical profession on ketone body analysis, resulting in the development of a plurality of procedures sensitive to the presence and/or concentrations of ketone bodies in urine.

But interest in monitoring the presence of ketones is by no means restricted to the medical profession. These compounds find a myriad of industrial applications - they are used as solvents in nitrocellulose coatings and vinyl films, they find applications in paint removers, cleaning fluids, organic synthesis, explosive manufacture, and as food additives—and in each there is a need at one time or another to perform an analytical procedure to determine ketone presence and/or concentration. These and numerous other concerns with respect to ketone presence have engendered many ketone tests.

One such test takes advantage of the propensity of ketones to react with sodium nitroprusside to give intense colors. Thus, acetone when treated with nitroprusside produces an intense red-yellow color which changes to pinkviolet on acidification with acetic acid [see Fritz Feigl, "Spot Test in Organic Analysis", 7th ed. (1966)]. This phenomenon occurs as a result of a coupling reaction through the NO group of the nitroprusside and the ketone to yield an isonitrosoketone which remains in the reaction mixture as a complex, colored anion. The iron (III) of the nitroprusside is reduced to its divalent state (II). It has been found that ketones which do not contain methyl or methylene groups bound to CO groups are not reactive, or at least they do not produce colorforms with nitroprusside.

The same or similar chemistry can be found in the ketone-sensitive portion of analytical reagent strips known as N-MULTISTIX ® KETO-DIASTIX ® and in the reagent tablet, ACETEST ®, all of which are marketed by the Ames Company Division of Miles Laboratories, Inc. All three of these devices for determining ketone bodies are based on the nitroprusside-ketone complexing phenomenon. Thus, when the reagent strips are immersed in aqueous ketone solution, or when the tablet is contacted with such a solution, the formation of a colored complex indicates the presence of a ketone. Moreover, the concentration of ketone can be estimated based on the intensity and hue of the color formed.

These and other methods for ketone body estimation require, as stated supra, a way of estimating their accuracy. One such approach is the use of a reference sample or control—a test sample in which the chemical composition and physical characteristics simulate the test samples to be analyzed. Hence, a control can be a urine sample which has been kept in the frozen state, or perhaps it comprises pooled urine which has been concentrated through freeze drying, later to be diluted to a predetermined volume.

Exemplary of a commercially available control is TEK-CHEK ®, marketed by the Ames Company, which utilizes the effect of a certain pH indicator in the presence of the buffering substance used in commercially available reagent strips having ketone-responsive reagent areas. Using this ketone substitute, TEK-CHEK produces a control solution which yields a positive test for ketones with the following Ames Company products: BILI-LABSTIX ®, LABSTIX ®, KETO-DIASTIX ®, KETOSTIX ®, MULTISTIX ®, N-MULTISTIX ® and ACETEST ®. TEK-CHEK is described in product literature available from the Ames Company as comprising lyophilized urine containing a chemical substitute for ketones. A substitute is used because ketones are difficult to retain in their natural state. Hence, TEK-CHEK utilizes a pH indicator to simulate a urine containing pathological amounts of ketone bodies.

Other commercially available ketone control solution products are marketed by Warner-Lambert Pharmaceutical Co. and American Hospital Supply Co., both of which products are liquids and both of which employ acetone as active agent for ketone.

U.S. Pat. No. 3,920,400, issued to Scheibe, et al., discloses a uric acid standard solution wherein a lithium salt of uric acid is employed as the control substance, and a complexing agent for polyvalent metals in their higher oxidation states is also present. Typical complexing agents are specified to be malonic acid, salicylic acid, oxalic acid, glutathione, cysteine, 8-oxyquinoline and ethylene-diaminetetracetic acid. The purpose of the complexing agent additive is to stabilize and prevent the decomposition of uric acid while in solution.

Still another example of a control is that disclosed in U.S. Pat. No. 3,920,580, issued to Mast and assigned to the present assignee. There is disclosed a liquid control for glucose determination in blood or serum. It comprises water, glucose and an antidifusing agent comprising a hydrophilic polymer.

Certain salts of cholesteryl hemisuccinate are described as being useful for cholesterol controls in U.S. Pat. No. 3,859,047.

To summarize the state of the art prior to the present invention, numerous control solution ingredients are known. TEK-CHEK solutions provide a substitute for ketones, a known pH indicator, which reacts with the buffering substances used in various ketone-responsive chemistries normally used in ketone determinations. No ketone compounds of their derivatives are employed as active ingredients. Other controls are equally known, such as for uric acid, glucose, cholesterol, and many others. Several liquid systems are presently marketed which contain acetone. None of the prior art controls, however, makes known the concepts presently disclosed and claimed. None discloses a ketone control device which utilizes the carrier vehicle or metal ion complex disclosed herein.

The present invention departs from the state of the art in dramatic fashion. No longer is it necessary to employ liquid formulations containing acetone or other liquid ketone. The present invention utilizes as an active ingredient diet a dry, easily storable material which, when dissolved, is directly reactive with the reagents of a ketone-sensitive test. The invention eliminates the need for liquid reagents and/or substitutes for ketones such as pH indicators responsive to the buffer of the ketone-sensitive reagent system. Thus, the invention provides a dry device, one which is stable upon storage and easily handled, and which provides ketone control solutions of remarkably accurate concentrations, ergo reproducibility with the ketone-sensitive test procedure.

SUMMARY OF THE INVENTION

Briefly stated, the present invention comprises a device for preparing a control solution for ketone analysis and a method for using it. The device comprises a carrier vehicle, such as a capsule or carrier matrix, incorporated with a metal ion complex of a dione compound. The dione compound has the structure

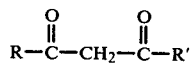

in which R and R', which can be the same or different, are alkyl groups having 1 to about 6 carbon atoms. The method comprises contacting a predetermined volume of solvent with the device.

DETAILED DESCRIPTION OF THE INVENTION

As used herein, the term "carrier vehicle" is intended to include any means suitable for transporting a specified amount of the metal ion complex. It includes a capsule, such as a gelatin capsule, capable of dissolving in water or otherwise openable to release its contents. It can comprise a perforated capsule such that solvent can enter the capsule when used, and leach out the metal ion/dione complex contained inside. It can also comprise foil or other material made into a sealed, easily openable package, the metal ion complex being sealed inside until eventual use, whereupon the package is opened and its contents emptied into a predetermined volume of water. Moreover, the carrier vehicle can comprise a carrier matrix comprising a wide range of materials. The carrier matrix is incorporated with the metal ion complex and, when used, is immersed in a predetermined volume of water for a predetermined time, and removed, leaving the metal ion complex behind in solution.

When a carrier matrix is utilized it can comprise any substance capable of being incorporated with the metal ion/dione complex. Thus the matrix can take on many known forms such as those utilized for reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Patent, No. 1,349,623, suggests the use of a light-permeable meshwork of thin filaments as a cover for an underlying paper matrix. This reference also suggests impregnating the paper with part of a reagent system and impregnating the meshwork with other potentially incompatible reagents. French Pat. No. 2,170,397 teaches the use of carrier matrices having greater than 50% polyamide fibers therein. Another approach to carrier matrices is disclosed in U.S. Pat. No. 4,046,513 wherein the concept of printing reagents onto a suitable carrier matrix is employed. U.S. Pat. No. 4,046,514 discloses the interweaving or knitting of filaments bearing reagents in a reactant system. All such carrier matrix concepts can be employed in the present invention, as can others. Preferably the carrier matrix comprises a bibuluous material such as filter paper.

The metal ion complex of the present invention is normally solid at temperatures up to room temperature and higher. Moreover it is sufficiently stable to enable storing for relatively long periods of time. It should be soluble in the system to be ultimately analyzed, such as an aqueous system. Finally, the dione compound forming part of the complex must be capable of producing a detectable response with the particular ketone analysis procedure contemplated.

The dione compounds are capable of forming complexes with the metal ions, the complexes having the above-described physical properties. It has been found that diones in which the carbonyl groups are separated by a methylene group are of particular utility. Thus compounds having the structure

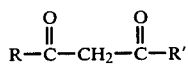

are preferred. R and R' can vary widely and can be methyl, ethyl, propyl, butyl, pentyl and hexyl, including isomers thereof. In addition, R and R' need not be the same. For example, R can be ethyl when R' is methyl, etc. Exemplary of dione compounds which satisfy these criteria are 2,4-propanedione (acetylacetone) in which R and R' are both methyl, 2,4-hexanedione in which R is methyl and R' is ethyl, and 3,5-heptanedione wherein R and R' are both ethyl. Nickel acetylacetonate has been found to be especially suitable as the metal ion complex.

The amount of metal ion/dione complex utilized in the present invention, i.e., incorporated with the carrier vehicle, depends upon several parameters. Firstly, each type of system in which ketone compound presence might be of analytical interest, be that system a paint formulation, urine, or other, demands an analytical system responsive to a certain range of ketone concentration. This concentration range will vary from system to system. Pathological urines, for example, necessitate that the ketone-sensitive area of N-MULTISTIX be responsive to ketone concentrations of from about 3 up to about 160 milligrams per deciliter. Accordingly, for a device for preparing a control solution for N-MULTISTIX reagent strips, an amount of metal ion/dione complex is required sufficient to provide a color change indicative of ketone concentrations in that range.

A second determining factor is the volume of control solution the device will ultimately be used to prepare. Thus if the device is incorporated with an amount of complex which when contacted with 30 milliliters of water will provide the desired N-MULTISTIX reagent strip response, that same device will provide too strong a response with 12 milliliters of water and too weak a response with 1 liter. Suffice it to say that the amount of complex incorporated with the carrier vehicle must be at least sufficient to provide the desired ketone concentration range in a predetermined amount of solvent. In urinalysis procedures, that concentration range is from about 0.1 to about 160 millimoles per liter.

The metal ions employed must be capable of forming complexes with the presently disclosed diones—complexes having the previously described physical properties of melting point, stability, and solubility. Typically suited are ions of aluminum (III), cobalt, copper (II), iron (III), magnesium, nickel and zinc. Particularly suitable is nickel.

EXAMPLES

The following Examples are provided to further illustrate preferred embodiments of the invention presently disclosed as claimed. As such, they are meant as being illustrative, and are not intended, nor are they to be construed, as limiting the scope of the claims appended hereto.

EXAMPLE I

CONTROL CAPSULES

A device for preparing a control solution which simulates human urine containing a pathological concentration of ketone was prepared. It comprised gelatin capsules containing, as active ingredient, nickel acetylacetonate. The ingredients employed were as follows:

| Ingredient | Grams |
|---|---|
| $Na_2HPO_4$ | 840.0 |
| Boric acid | 900.0 |
| Nickel acetylacetonate | 60.0 |
| Lactose | 916.2 |
| Sodium lauryl sulfate | 4.8 |

The $Na_2HPO_4$ and boric acid were dried in an air oven at about 150° F. for 16 hours, and the nickel acetylacetonate and sodium lauryl sulfate were mixed thoroughly with a mortar and pestle. These ingredients were then combined with the lactose on tray paper and added to a 1.0 cubic foot, twin shell, dry V-Blender manufactured by Patterson-Kelly Company, and blended for about 20 minutes.

The blended ingredients were then used to prepare control capsules. Six thousand clear gelatin capsules, size No. 0, obtained from Eli Lilly and Company were charged with the ingredients using a number 8 capsule filling machine obtained from Parke, Davis and Company. The resultant capsule each contained 1 milligram of acetylacetonate.

EXAMPLE II

Preparation of a Ketone Control Solution and Use with N-MULTISTIX ® Reagent Strips A control capsule prepared as in Example I was used to prepare a ketone control solution responsive to the ketone test area of an N-MULTISTIX ® reagent strip marketed by the Ames Company Division of Miles Laboratories, Inc.

The contents of one capsule were added to 30 ml. deionized water and thoroughly mixed. An N-MULTISTIX reagent strip was momentarily immersed in the solution and the ketone-responsive reagent area observed for a color response. A positive response for ketone was indicated by the appearance of a purple color.

EXAMPLE III

Control Capsule

A device somewhat similar to that of Example I was prepared for use with a CLINI-TEK ® reflectance photometer, marketed by the Ames Company Division of Miles Laboratories, Inc. Accordingly, clear gelatin capsules were filled with the various ingredients listed below.

| Ingredient | Grams/1000 capsules |
|---|---|
| $Na_3PO_4$ | 145.0 |
| Boric acid | 35.0 |
| Nickel acetylacetonate | 2.36 |
| Lactose | 246.03 |
| Sodium lauryl sulfate | 0.32 |

The sodium phosphate and boric acid were thoroughly dried in an air oven at about 150° F., and the nickel acetylacetonate and sodium lauryl sulfate were comminuted in a mortar and pestle. These ingredients were then combined with the lactose on tray paper and blended in the V-Blender of Example I for about 20 minutes.

The blended ingredients were then used to prepare ketone control capsules. One thousand clear gelatin capsules, size No. 0, obtained from Eli Lilly and Company were uniformly charged with the ingredients using a number 8 capsule filling machine obtained from Parke, Davis and Company. The resultant capsules each contained 2.36 milligrams of nickel acetylacetonate.

EXAMPLE IV

Preparation of a Ketone Control Solution and its Use with CLINI-TEK ® Reflectance Photometer A control capsule prepared as in Example III was used to prepare a ketone control solution responsive to the ketone test area of CLINI-TEK TM reagent strips, which strips are designed for use in conjunction with a CLINI-TEK ® reflectance photometer. The ketone test portion of the CLINI-TEK reagent strips utilizes chemistry similar to that of the ketone test portion of N-MULTISTIX reagent strips.

The contents of one capsule were added to 12 milliliters of deionized water and thoroughly mixed. A CLINI-TEK reagent strip was immersed in the solution and removed, and the wet strip inserted in the CLINI-TEK ® reflectance photometer. The instrument gave a reading of 3+ for ketone, indicating proper instrument response. Should the instrument read other than the predetermined 3+ response, it can be adjusted accordingly.

EXAMPLE V

Immersible Strip Ketone Control Device

A device for the preparation of a control solution simulating human urine containing a pathological concentration of ketone was prepared. A strip of filter paper (Eaton & Dikeman No. 222) was immersed in a solution of 0.5 grams nickel acetylacetonate in 50 milliliters of water and dried at about 180° F. for about 15 minutes. The resultant impregnated dried paper was cut into rectangles measuring 0.2 by 0.4 inches. These rectangles were mounted on one end of strips of polystyrene (Trycite ® from Dow Chemical Co.) measuring about 0.2 by 4 inches, using double-faced adhesive tape (Double Stick from 3M Co.) to provide a ketone control device.

EXAMPLE VI

Preparation of a Ketone Control Solution and Use with N-MULTISTIX ® Reagent Strips A device from Example V was immersed in 5 milliliters of deionized water for about 15 minutes and then removed, thus preparing a ketone control solution simulating a urine containing a pathological amount of ketone.

The control solution thus prepared was then tested with the ketone-sensitive reagent area of an N-MULTISTIX reagent strip. A purple color developed in the ketone area indicative of a moderate elevation of ketone bodies in urine.

EXAMPLE VII

Control Device Using Cupric Acetylacetonate

Gelatin capsules are prepared as in Example I except that 61.18 grams cupric acetylacetonate are substituted for nickel acetylacetonate. This ketone control device and the capsules in Example I have a substantially equimolar dione content.

EXAMPLE VIII

Control Device Using Aluminum (III) Acetylacetonate

Gelatin capsules are prepared as in Example I except that 50.54 grams aluminum (III) acetylacetonate are substituted for the nickel acetylacetonate. This device and the capsules of Example I have a substantially equimolar dione content.

EXAMPLE IX

Control Device Using Iron (III) Acetylacetonate

Gelatin capsules are prepared as in Example I except that 55.0 grams iron (III) acetylacetonate are substituted for nickel acetylacetonate. This device and those of Example I have a substantially equimolar dione content.

EXAMPLE X

Control Device Using Zinc Acetylacetonate

Gelatin capsules are prepared as in Example I except that 61.6 grams of zinc acteylacetonate are substituted for nickel acetylacetonate. This device and those capsules of Example 1 have a substantially equimolar dione content.

EXAMPLES XI–XIV

Immersible Strip Ketone Control Device Utilizing Various Metal Ion/Dione Complexes Immersible strip devices are prepared as in Example V except that the nickel acetylacetonate in the 50 milliliters of water solution is replaced by the amounts of acetylacetonate complexes tabulated below:

| Example | Metal Ion Complex | Grams in Solution |
|---|---|---|
| XI | Cupric Acetylacetonate | 0.51 |
| XII | Aluminum (III) Acetylacetonate | 0.42 |
| XIII | Iron (III) Acetylacetonate | 0.46 |
| XIV | Zinc Acetylacetonate | 0.51 |

The strips prepared in each of Examples V and XI–XIV contain substantially equimolar amounts of dione.

What is claimed is:

1. A device useful in the preparation of a ketone control solution, said device comprising a carrier vehicle incorporated with a predetermined quantity of a metal ion complex of a dione compound, said metal ion being aluminum (III), cobalt, copper (II), iron (III), magnesium, nickel or zinc, and said dione compound having the structure

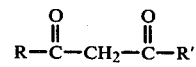

in which R and R', same or different, are alkyl groups having 1 to about 6 carbon atoms.

2. The device of claim 1 wherein said dione compound is acetylacetone.

3. The device of claim 1 wherein said complex is nickel acetylacetonate.

4. The device of claims 1, 2 or 3 wherein said carrier vehicle is a capsule containing said complex, said capsule comprising a water soluble substance.

5. The device of claim 4 wherein said water soluble substance is gelatin.

6. The device of claim 1, 2 or 3 wherein said carrier vehicle is a bibulous material impregnated with said complex.

7. The device of claim 6 wherein said carrier vehicle is paper.

8. The device of claim 1 wherein said carrier vehicle is paper and said metal complex is nickel acetylacetonate.

9. A device useful in the preparation of a ketone control solution, said device comprising
   a carrier matrix incorporated with a predetermined amount of a composition comprising a metal ion complex of acetylacetone wherein said metal ion is aluminum (III), cobalt, copper (II), iron (III), magnesium, nickel or zinc and
   a support member comprising an elongated plastic strip having said carrier matrix affixed thereto.

10. The device of claim 9 wherein said metal complex is nickel acetylacetonate.

11. A method for preparing a ketone control solution, comprising contacting a predetermined volume of solvent with the device of claim 1, 2, 3, 9 or 10.

12. A method for preparing a ketone control solution, comprising contacting a predetermined volume of solvent with the device of claim 4.

13. A method for preparing a ketone control solution, comprising contacting a predetermined volume of solvent with the device of claim 6.

14. A method for preparing a ketone control solution, comprising contacting a predetermined volume of solvent with the device of claim 5.

15. A method for preparing a ketone control solution, comprising contacting a predetermined volume of solvent with the device of claim 7.

16. A method for preparing a ketone control solution, comprising contacting a predetermined volume of solvent with the device of claim 8.

17. A method for calibrating a ketone test instrument comprising contacting a predetermined amount of solvent with the device of claim 1, 2, 3, 9 or 10 to form a control solution normally capable of producing a predetermined response in said instrument when contacted therewith, contacting said control solution with said instrument, observing the actual response in said instrument, comparing said actual response with said predetermined response, and adjusting said instrument to provide said predetermined response.

18. A method for calibrating a ketone test instrument comprising contacting a predetermined amount of solvent with the device of claim 4 to form a control solution normally capable of producing a predetermined response in said instrument when contacted therewith, contacting said control solution with said instrument, observing the actual response in said instrument, comparing said actual response with said predetermined response, and adjusting said instrument to provide said predetermined response.

19. A method for calibrating a ketone test instrument comprising contacting a predetermined amount of solvent with the device of claim 6 to form control solution normally capable of producing a predetermined response in said instrument when contacted therewith, contacting said control solution with said instrument, observing the actual response in said instrument, comparing said actual response with said predetermined response, and adjusting said instrument to provide said predetermined response.

20. A method for calibrating a ketone test instrument comprising contacting a predetermined amount of solvent with the device of claim 5 to form a control solution normally capable of producing a predetermined response in said instrument when contacted therewith, contacting said control solution with said instrument, observing the actual response in said instrument, comparing said actual response with said predetermined response, and adjusting said instrument to provide said predetermined response.

21. A method for calibrating a ketone test instrument comprising contacting a predetermined amount of solvent with the device of claim 7 to form a control solution normally capable of producing a predetermined response in said instrument when contacted therewith, contacting said control solution with said instrument, observing the actual response in said instrument, comparing said actual response with said predetermined response, and adjusting said instrument to provide said predetermined response.

22. A method for calibrating a ketone test instrument comprising contacting a predetermined amount of solvent with the device of claim 8 to form a control solution normally capable of producing a predetermined response in said instrument when contacted therewith, contacting said control solution with said instrument, observing the actual response in said instrument, comparing said actual response with said predetermined response, and adjusting said instrument to provide said predetermined response.

23. A method for preparing a ketone control solution comprising contacting a predetermined volume of solvent with a predetermined quantity of metal ion complex of a dione compound, said metal ion being aluminum (III), cobalt, copper (II), iron (III), magnesium, nickel or zinc, and said dione compound having the structure

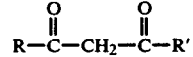

in which R and R', same or different, are alkyl groups having 1 to about 6 carbon atoms.

24. The method of claim 23 wherein said dione compound is acetylacetone.

25. The method of claim 23 wherein said metal complex is nickel acetylacetonate.

* * * * *